United States Patent
Drumm et al.

(10) Patent No.: US 8,162,955 B2
(45) Date of Patent: Apr. 24, 2012

(54) REGISTERING INTRAOPERATIVE SCANS (75) Inventors: Peter Drumm, Munich (DE); Gunther Becht, Dornach (DE)

(73) Assignee: Brainlab AG, Feldkirchen (DE)

( * ) Notice: Subject to any disclaimer, the term of this patent is extended or adjusted under 35 U.S.C. 154(b) by 970 days.

(21) Appl. No.: 11/219,325

(22) Filed: Sep. 2, 2005

(65) Prior Publication Data

US 2006/0084889 A1 Apr. 20, 2006

Related U.S. Application Data (60) Provisional application No. 60/609,581, filed on Sep. 14, 2004.

(30) Foreign Application Priority Data

Sep. 2, 2004 (EP) .................................... 04020839

(51) Int. Cl.
*A61B 19/00* (2006.01)
(52) U.S. Cl. .......................... 606/130; 600/407; 600/587
(58) Field of Classification Search .................. 600/587; 606/151, 130
See application file for complete search history.

(56) References Cited

U.S. PATENT DOCUMENTS

| | | | |
|---|---|---|---|
| 4,341,220 A | 7/1982 | Perry | |
| 4,624,245 A | 11/1986 | Mullin et al. | |
| 5,249,581 A * | 10/1993 | Horbal et al. | 600/407 |
| 5,327,907 A | 7/1994 | Fischer | |
| 5,681,326 A | 10/1997 | Lax | |
| 6,143,003 A | 11/2000 | Cosman | |
| 6,499,488 B1 | 12/2002 | Hunter et al. | |
| 6,925,339 B2 * | 8/2005 | Grimm et al. | 700/59 |
| 2003/0153829 A1 * | 8/2003 | Sarin et al. | 600/426 |
| 2004/0102792 A1 * | 5/2004 | Sarin et al. | 606/151 |
| 2004/0210233 A1 * | 10/2004 | Yoon et al. | 606/102 |
| 2004/0267284 A1 | 12/2004 | Parmer et al. | |
| 2005/0075632 A1 * | 4/2005 | Russell et al. | 606/53 |
| 2005/0076441 A1 * | 4/2005 | Dominati et al. | 5/621 |
| 2006/0084889 A1 | 4/2006 | Drumm et al. | |

FOREIGN PATENT DOCUMENTS

| | | | |
|---|---|---|---|
| CH | 240449 | | 12/1945 |
| DE | 634127 | | 8/1936 |
| EP | 1292235 | * | 3/2003 |
| EP | 1522300 | * | 10/2003 |
| EP | 1 632 193 | | 3/2006 |
| WO | 01/21084 A1 | | 3/2001 |
| WO | WO 01/21084 | * | 3/2001 |
| WO | WO0191647 | * | 6/2001 |

OTHER PUBLICATIONS

European Search Report for corresponding Application No. 04020839.9 dated Jan. 18, 2005.

* cited by examiner

*Primary Examiner* — Max Hindenburg
*Assistant Examiner* — Renee Danega
(74) *Attorney, Agent, or Firm* — Renner, Otto, Boisselle & Sklar, LLP (57) ABSTRACT

A device and method for registering a patient's hip, wherein the device includes markers and positioning elements which can be placed on characteristic points of the hip, and once placed on characteristic points of the hip, data for registering the hip can be ascertained from the position of the markers. The method includes detecting the position of the markers arranged on the device and ascertaining data for registering the hip.

22 Claims, 10 Drawing Sheets

REGISTERING INTRAOPERATIVE SCANS

RELATED APPLICATION DATA

This application claims priority of U.S. Provisional Application No. 60/609,581 filed on Sep. 14, 2004, which is incorporated herein by reference in its entirety.

FIELD OF THE INVENTION

The present invention relates to a registration of a body part in a medical navigation system. More particularly, the invention relates to a apparatus, system and method for registering (i.e. determining the spatial position of) the hip or pelvic bone, for example, in preparation for a surgical incision.

BACKGROUND OF THE INVENTION

Figure 9:
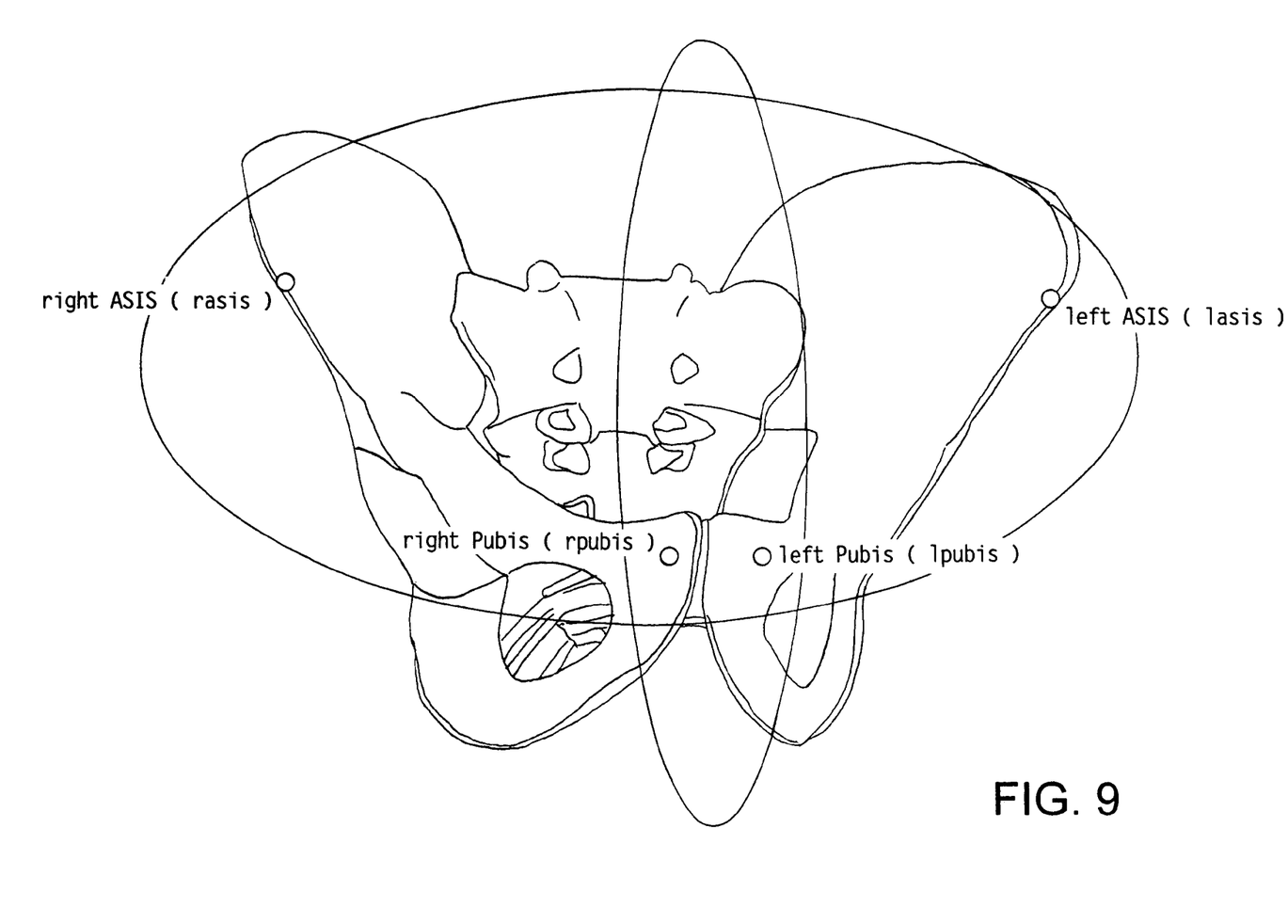
FIG. 9 is a schematic representation of the pelvic bones, with the mid-sagittal plane and the pelvic inlet plane indicated.

In order to prepare for a surgical incision in the region of the hip and, in particular, in an operation on the pelvic bone (e.g., in the region of the hip joint) such as when inserting a hip joint cavity, it is necessary for the hip to be registered, i.e., for the spatial position of the hip or pelvic bone to be detected. When registering the hip, the spatial position of the mid-sagittal plane, which is a plane of symmetry of the pelvis, and the pelvic inlet plane or anterior pelvic plane, which is defined by two spinal points and a pubic point, can be ascertained. One spinal point, also commonly referred to as the ASIS (anterior or superior iliac spine), is a characteristic point or anatomical landmark on the pelvic bone and can be easily located on the pelvic bone. The left-side spinal point (lasis) and right-side spinal point (rasis) are indicated in FIG. 9. A pubic point is a characteristic point on the mons pubis of the pelvic bone and is indicated in FIG. 9 by rpubis for the pubic point of the right-side pelvic bone and by lpubis for the pubic point of the left-side pelvic bone.

In order to register the hip, the patient is placed in a supine position and the positions of the spinal and pubic points are palpated by a surgeon. These points can be communicated to navigation software by a pointer provided with markers that can be detected by a camera. Once the corresponding points have been recorded with the patient in the supine position, the patient is placed in a lateral position in order to make a surgical incision in the region of the right-side or left-side pelvic bone, such as, for example, to insert an artificial hip joint cavity, the position of which is defined by the position of the mid-sagittal plane and the anterior pelvic plane as defined by the spinal and pubic points.

If inaccuracies arise while determining the spinal and pubic points, or there is a change in the position of the pelvic bones while turning the patient from the supine to the lateral position, then an inaccuracy may result when inserting an artificial hip joint. This can lead to complications arising for the patient, for example, because the incorrect positioning of the artificial hip joint can cause pain. Similarly, a hip joint cavity can be subject to a high degree of wear due to improper positioning, such that the service life of the implant is reduced.

SUMMARY OF THE INVENTION

The present invention provides a device that enables a hip to be registered in a lateral patient position. Consequently, a patient no longer has to be turned from the supine position to the lateral position once the hip has been registered. The device comprises markers, such as, for example, four passive markers that can be formed by reflective surfaces or spheres. The device further comprises positioning elements, such as, for example, three or four rods having a conically tapered or pointed end that can be placed on characteristic points of the hip (e.g., spinal points (ASIS) and pubic points) in order to register the hip. The markers attached to the device can be in a defined and known positional relationship to the positioning elements or the tips/ends of the rods. The positioning elements thus do not have to come into direct contact with the pelvic bone. For example, the positioning elements can be placed on a patient's skin, through which the characteristic points can be palpated. With such a device, it is possible via the position of the markers connected to the device to determine the course or spatial position of the mid-sagittal plane and the pelvic inlet plane, whereby the hip can be registered. Markers also can be advantageously affixed to the hip or pelvic bone.

It is possible via the spatial position of placement points of the positioning elements to the positions of the markers connected to the device to determine the position of one or both spinal points and one or both pubic points of the pelvic bones. Based on these points, the spatial position of the mid-sagittal plane as the plane of symmetry and the spatial position of the pelvic inlet plane (which can be defined by the position of two spinal points and a pubic point) can be determined. Thus, the hip can be registered in a lateral patient position without taking x-ray recordings, wherein the patient is advantageously stably positioned. Preferably, the patient is substantially fixed in the region of the hip in a lateral position by a supporting device such as, for example, by two padded plates or a framework.

In order to register a patient's hip or pelvic bones, the device can be affixed to a supporting device for positioning the patient in the lateral position. The device then can be positioned on the patient, and the positioning elements connected to the device can be shifted in such a way that they are lying on or are placed on characteristic points of the pelvic bones. From this data, the position of the mid-sagittal plane and the pelvic inlet plane can be determined on the basis of the markers connected to the device. Once the hip has been registered, the device in accordance with the invention can be removed from the supporting device, such that a surgical incision can be made, for example, in order to insert a joint cavity. The alignment of the joint cavity can be defined by the position of the mid-sagittal plane and the pelvic inlet plane. These planes can be determined using the device, wherein an angle in which a normal of the joint cavity forms with the mid-sagittal plane is referred to as the inclination and an angle in which the normal of the joint cavity forms with the pelvic inlet plane is referred to as the anteversion. The joint cavity can be positioned such that these angles, which vary from patient to patient, have a desired value of 45 degrees (inclination) and 15 degrees (anteversion), for example.

The position of the markers arranged on the device can be detected using known navigation systems, such as VectorVision®, for example, by means of infrared cameras. Such navigation systems are well known by those having ordinary skill in the art and, therefore, will not be described herein.

The device can be a framework, a frame or simply a plate, for example, on which positioning elements, such as four rods, are arranged fixed or such that they can be shifted. The distance between two positioning elements that are to be placed on the spinal points can be changed, for example, using an adjusting element, wherein one positioning element is fixedly connected to the device and the other positioning element can be moved relative to the device. It is equally possible for both positioning elements to be movable relative to the device. For example, the positioning elements can be shifted along guides in the device, wherein a defined point on the device is pre-set, at which a marker also can be arranged. Preferably, the marker always lies on a midpoint between the two positioning elements. A mechanism can ensure that when one positioning element is shifted, the other element is moved in the opposite direction. Correspondingly, the positioning elements that are to be placed on the pubic points also can be connected to the device in a fixed configuration or such that they can be shifted. The positioning elements also can comprise a mechanism that enables the positioning elements to always be moved symmetrically and/or synchronously with respect to a defined center point to which a marker can be attached. A mechanism that enables the positioning elements to be moved synchronously and/or synchronously with respect to a center point is advantageous for registering a hip since, for example, markers can be attached to these center points and the mid-sagittal plane, which passes through the easily determinable positions of these markers, can be determined.

Generally speaking, the markers can be attached to any desired position of the device and/or positioning elements (which can be detected by a camera). Preferably, the markers exhibit a defined or definable positional relationship to the device and/or to the positioning elements connected to the device. The defined positional relationship, via a database in which the geometry of the device and adjusting options of the positioning elements are stored, facilitates the determination of a position of the placement points of the positioning elements once the spatial position of the markers has been ascertained.

A known reference star, to which three markers are attached, can be connected to the device, wherein a star plane, i.e., the plane in which the markers connected to the star lie, is advantageously parallel to a plane defined by the four placement points of the four positioning elements. Preferably, the positioning elements then can be moved by a guide in the device in such a way that their placement points always move within a plane that defines the pelvic inlet plane (anterior pelvic plane) when the device is placed on the pelvic bone. More specifically, when the distance between the star plane and the plane defined by the placement points of the positioning elements is known, i.e., the device in accordance with the invention is pre-calibrated, the position of the pelvic inlet plane can be easily ascertained from the detected positions of the markers connected to the star.

Preferably, the distance of a pair of positioning elements that can be placed on the spinal points from a pair of positioning elements to be placed on the pubic points can be changed. A pair of positioning elements advantageously can be shifted such that a line defined by the contact points of a pair of positioning elements is always parallel to a line defined by the contact points of the other pair of positioning elements. For example, one pair of positioning elements can be guided in the device such that the distance between the positioning elements can be changed. Further a second pair of positioning elements can be arranged on a carriage that can be shifted relative to the device and wherein the distance between the positioning elements arranged on the carriage and guided in the carriage also can be changed.

It is also possible for individual markers to be attached to the device itself and/or to one or more adjusting elements (which can be shifted). For example, a marker can be attached to each positioning element, such that if four positioning elements are used, a total of four markers are provided. It is equally possible for markers to be attached only to two positioning elements and for another marker to be arranged centrally between two positioning elements in each case, e.g., on a setting element such as a turning wheel that is used to adjust a distance between two markers. The positioning elements can be advantageously positioned in the device such that they can be shifted while an angle formed by the two markers connected fixedly to the device and another marker is always 90 degrees.

A marker and/or reference star also can be connected to the device by an adjustable marker array such as is described in the European patent application having the application number 04 003 019.9 and the corresponding U.S. provisional application No. 60/548,153, the contents of which is incorporated by reference in its entirety. An adjustable marker array, such as in the cited specifications, enables one or more markers or a reference star to be connected to the device or to one or more positioning elements such that the marker array can be moved independently of the movement of the device or the positioning element, without losing the spatial assignment of one or more markers to the elements connected to the marker or markers.

The invention also provides a system for registering a patient's hip, comprising a device as described above, a detection apparatus, such as, for example, an infrared camera, for detecting the position of the markers connected to the device, and a computational unit connected to the detection device. The system can ascertain the position of the contact points of the positioning elements and therefore the position of the spinal points and pubic points from the detected position of the markers. From this the system can determine the position of the mid-sagittal plane and the pelvic inlet plane. The computational unit can be advantageously connected to a database in which the geometry of one or more devices in accordance with the invention is stored. This permits the use of different devices, wherein the position of the positioning elements can be calculated from the position of the markers.

The computational unit can be advantageously connected to an output unit, such as a screen or the like, on which the position of the mid-sagittal plane and the pelvic inlet plane ascertained using the system in accordance with the invention can be displayed, as shown in FIG. 9, for example.

The invention also provides a method for registering a hip using a device as described above, wherein placement points of the positioning elements can be placed on characteristic points of the pelvic bones, the positions of the markers connected to the device can be detected, and the positions of the placement points of the positioning elements can be determined from the detected positions of the markers.

The invention further provides a computer program which, when it is loaded onto a computer or is running on a computer, performs such a method. The invention further provides a program storage medium or a computer program product comprising such a program.

The invention will be described below on the basis of preferred exemplary embodiments.

DETAILED DESCRIPTION

Figure 1A:
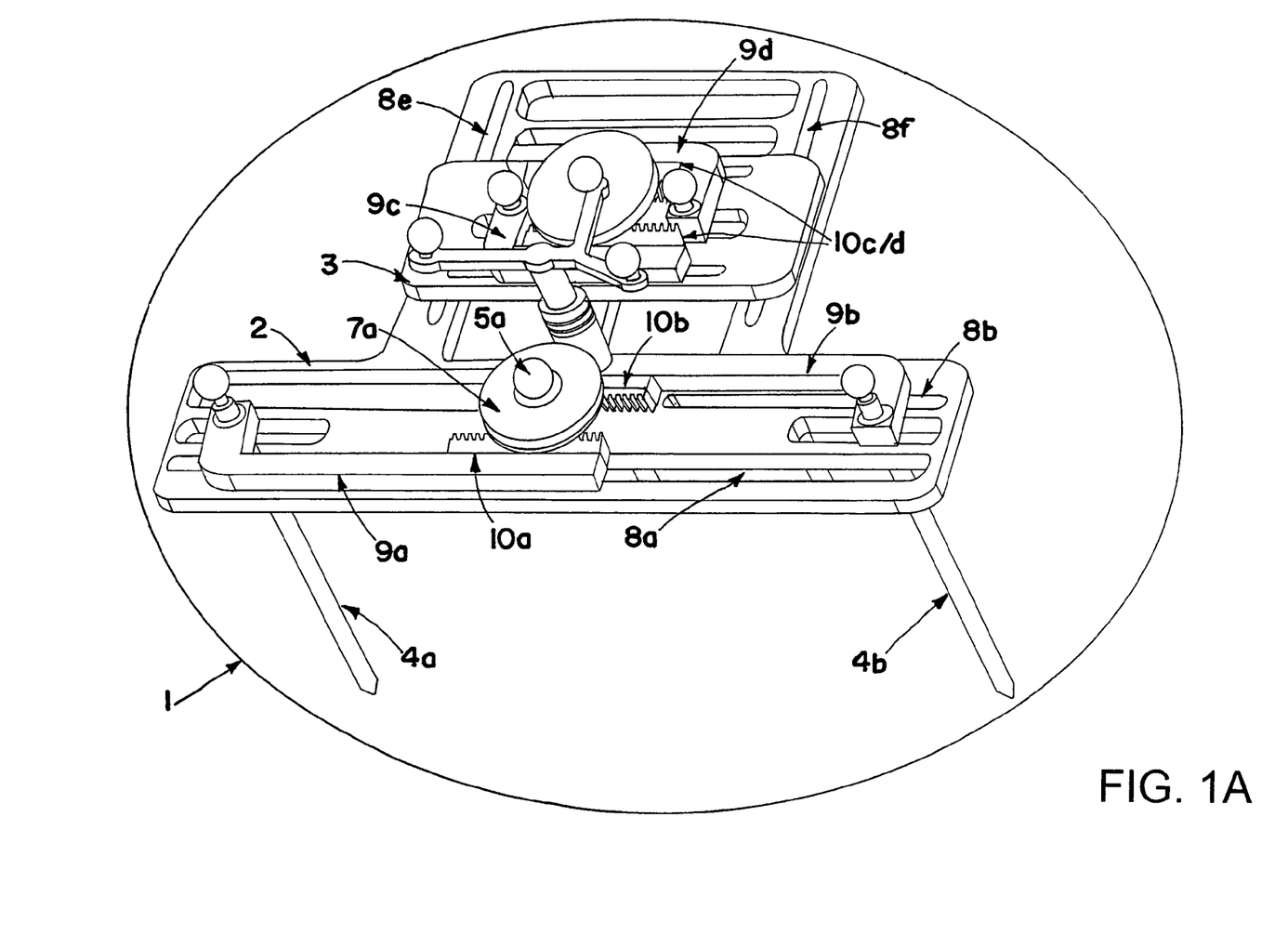
FIGS. 1A and 1B show a first embodiment of a device in accordance with the invention.
Figure 1B:
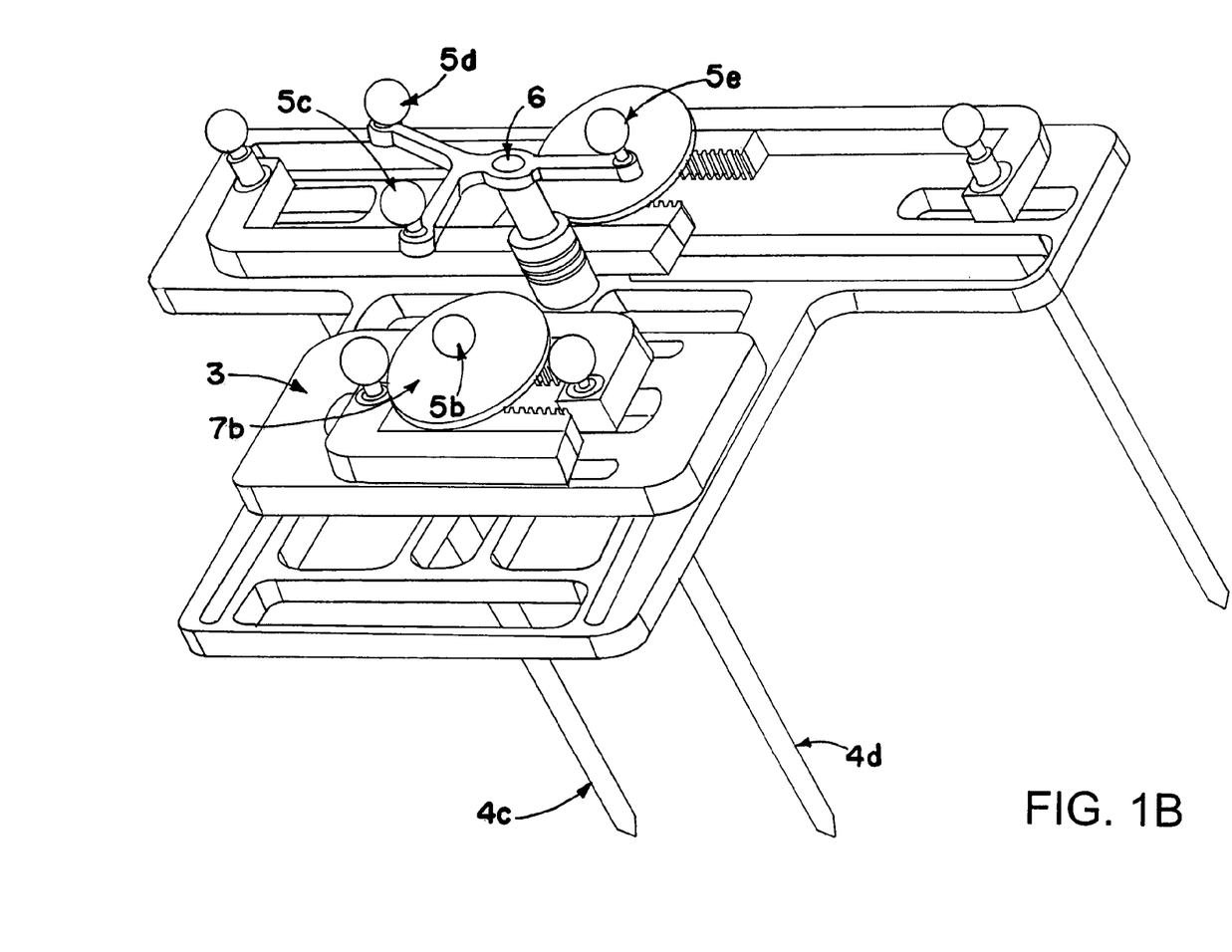

FIGS. 1A and 1B show a hip registration device 1 that can be placed on a patient in a lateral position or in a supine position. The device 1 includes a plate 2 in which guides 8a and 8b formed as slits are provided for guiding two positioning elements 4a and 4b. The positioning elements 4a and 4b are held by mountings 9a and 9b which each include a toothed rod 10a and 10b opposite each other. The toothed rods 10a and 10b engage with a toothed wheel (not shown) below an adjusting element 7a, such that turning the adjusting element 7a causes the two positioning elements 4a and 4b to uniformly and oppositely move away from or towards the adjusting element 7a. Preferably, a center point of the adjusting element 7a always lies on the midpoint between the positioning elements 4a and 4b. A reflective spherical marker 5a is attached to the adjusting element 7a.

The plate 2 further includes guides 8e and 8f for guiding a carriage 3 on which two mountings 9c and 9d provided with toothed rods 10c and 10d are arranged, also adjustable via a second adjusting element 7b. The mountings 9c and 9d are connected to positioning elements 4c and 4d, wherein the positioning elements 4c and 4d positioned on the carriage 3 can be shifted by turning the adjusting element 7b, such that a marker 5b arranged on the adjusting element 7b always lies on the midpoint between the two positioning elements 4c and 4d.

The carriage 3 can be moved along the guides 8e and 8f, away from or towards the positioning elements 4a and 4b, wherein the positioning elements 4a to 4d are positioned or guided such that the positioning elements formed as rods are always approximately parallel to each other. Further, a line formed by the undersides of the positioning elements 4a and 4b (the undersides of positioning elements 4a and 4b serving as contact points) is always parallel to a line formed by the undersides of the positioning elements 4c and 4d (the undersides of positioning elements 4c and 4d serving as contact points).

A reference star 6 including three reflective markers 5c, 5d and 5e is affixed to the plate 2, wherein a star plane (the plane formed by the three reflective markers 5c, 5d and 5e) is parallel to a plane defined by the undersides of the positioning elements 4a to 4d. The positioning elements 4a to 4d of the registration device 1 thus can be moved such that they can be placed on the characteristic points of a substantially symmetrically formed hip, as shown in FIG. 2.

Figure 2:
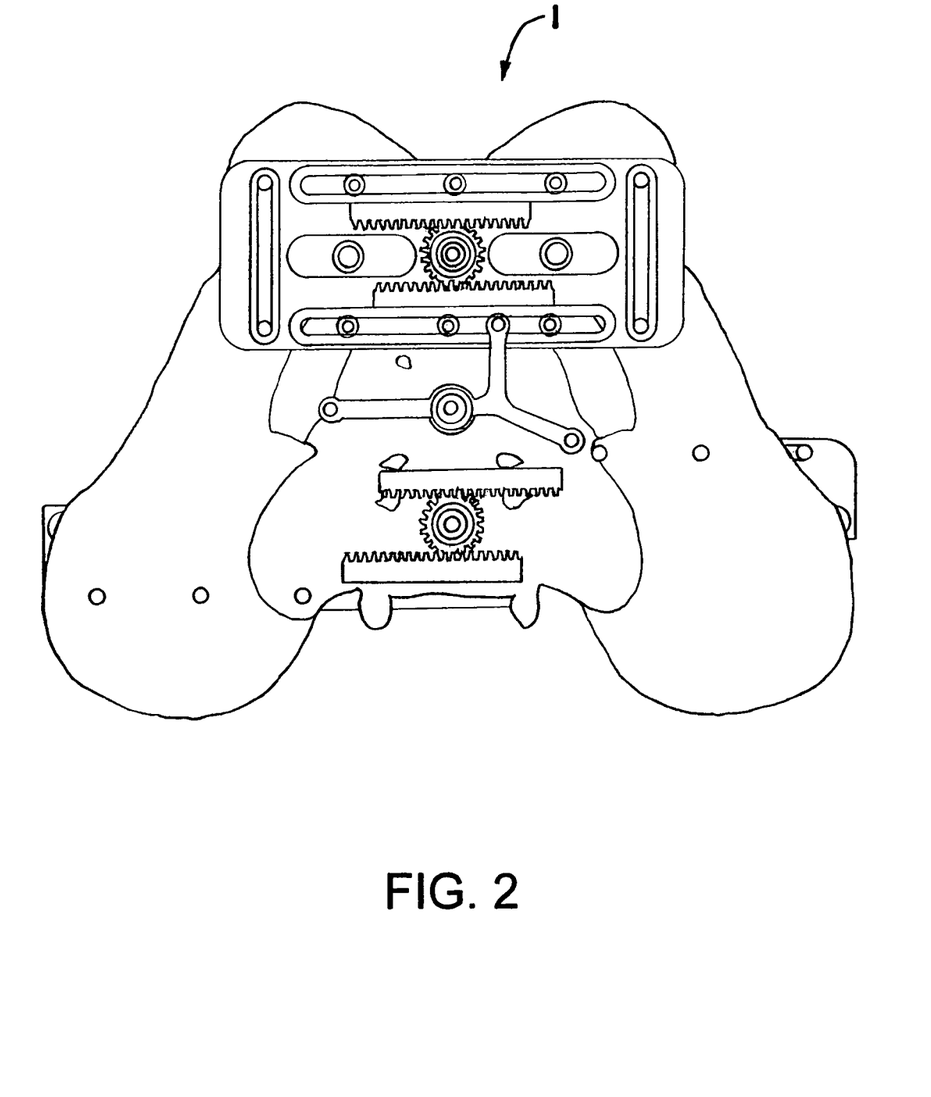
FIG. 2 illustrates the device in accordance with FIG. 1 placed on pelvic bones.
Figure 3:
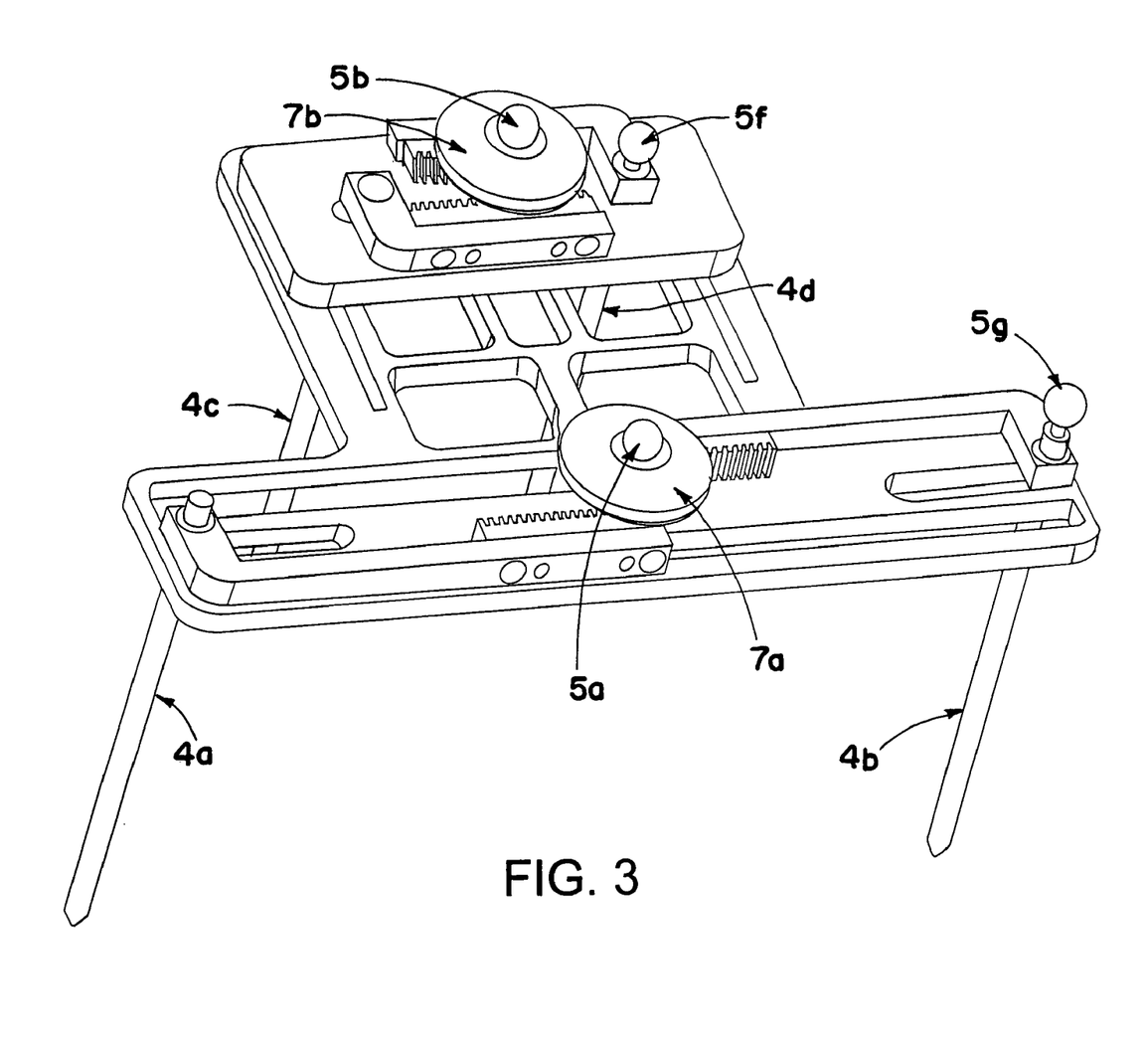
FIG. 3 illustrates a second embodiment of a device in accordance with the invention.

FIG. 3 shows a second embodiment in accordance with the invention, wherein, as opposed to the first embodiment shown in FIG. 1 and FIG. 2, a reference star 6 is not provided. Rather, markers 5f and 5g are provided on two positioning elements 4b and 4d, which are placed on a spinal point and a pubic point.

Figure 4:
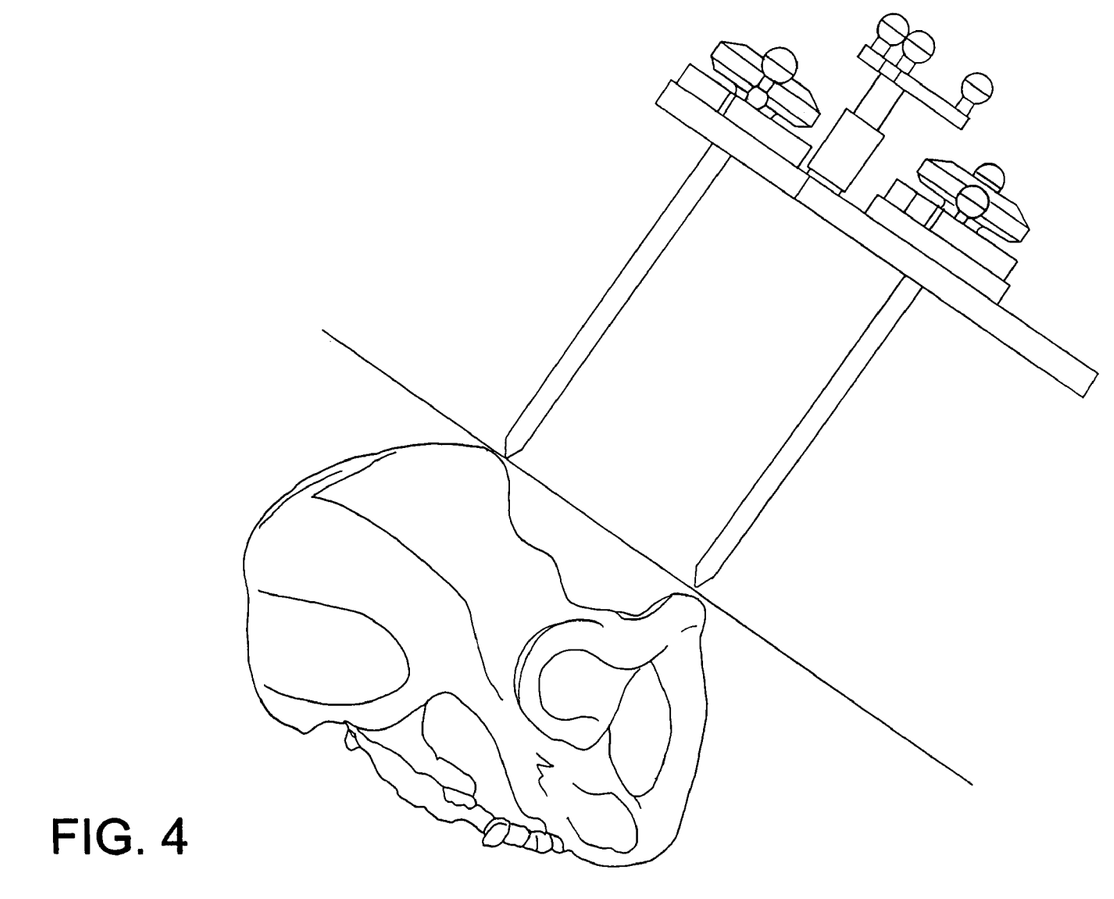
FIG. 4 is a lateral view of a device in accordance with the first embodiment of the invention, placed on a pelvis.

If the positioning elements 4 have been placed on characteristic points of a hip, as shown in FIG. 4 for a device in accordance with the first embodiment, then the placement points of the positioning elements 4a to 4d are used to determine the pelvic inlet plane. The pelvic inlet plane can be easily ascertained if the plane of the reference star 6 lies parallel to the plane formed by the contact points of the positioning elements 4 and the geometry of the registration device 1 is known, e.g., the distance of the plane of the reference star 6 from the plane formed by the positioning elements 4 is known. The mid-sagittal plane can be ascertained from the position of the markers 5a and 5b arranged on the adjusting elements 7a and 7b and the position of another marker of the reference star. The position of the mid-sagittal plane and the pelvic inlet plane thus can be determined, whereby the position of the pelvic bone is known and the hip is registered.

It is equally possible to register a hip using the device shown in FIG. 3, wherein just as with the device shown in FIGS. 1 and 2, the positioning elements 4a to 4d are placed on the spinal points and pubic points and the position of the markers 5a, 5b, 5g and 5f is ascertained. If the geometry of the device is known and if the markers 5a, 5b, 5g and 5f lie in a plane that is parallel to the plane defined by contact points of the positioning elements 4a to 4d, then the position of the pelvic inlet plane can be ascertained from the detected position of the markers 5a, 5b, 5f and 5d. Similarly, the mid-sagittal plane passing through the markers 5a and 5b can be ascertained if the position of the markers 5f and 5g is taken into account, in particular if the markers 5a, 5b, 5f and 5b, 5a, 5g each define a right angle.

Figure 5:
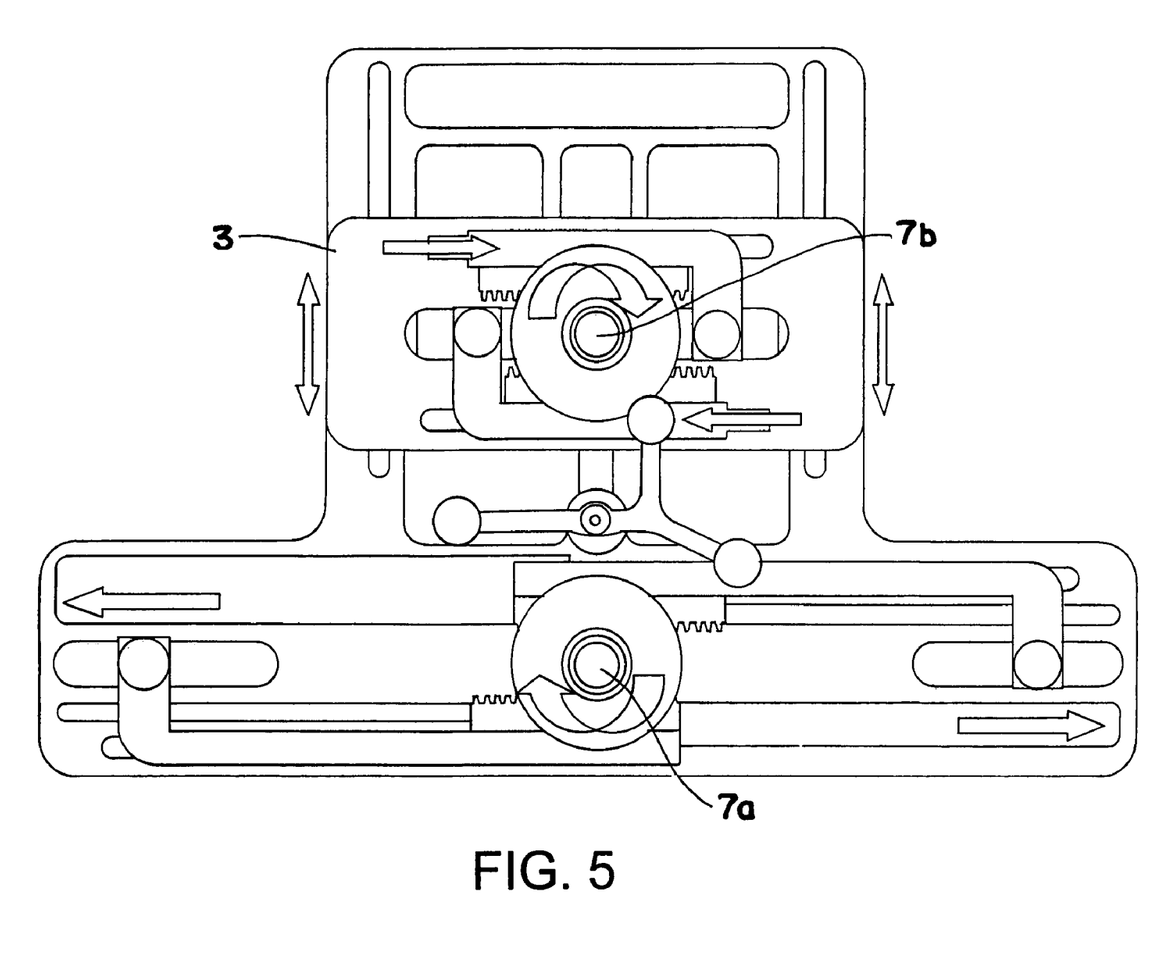
FIGS. 5 and 6 illustrate the device in accordance with a second embodiment, during a setting procedure.

FIG. 5 shows the device of FIG. 3 during a setting procedure, wherein firstly the rods or pins 4a and 4b (serving as the positioning elements) are placed on the spinal points (ASIS) of the hip. The distance of the pins 4a and 4b from each other can be set by turning the adjusting element 7a, wherein the two pins 4a and 4b move synchronously, such that the setting element 7a and the marker 5a arranged on it always lie on the midpoint between the two pins 4a and 4b. The distance between the pins 4c and 4d to be placed on the pubic points then is set by turning the adjusting element 7b. If it is not possible to place the tips of the pins 4c and 4d exactly on both pubic points, only the pubic point of the side to be treated can be marked, e.g., the pin which is not on the side to be treated does not lie on a pubic point. The distance between the "ASIS line" defined by the pins 4a and 4b and the "pubic line" defined by the pins 4c and 4d then is set by shifting the carriage 3.

Figure 6:
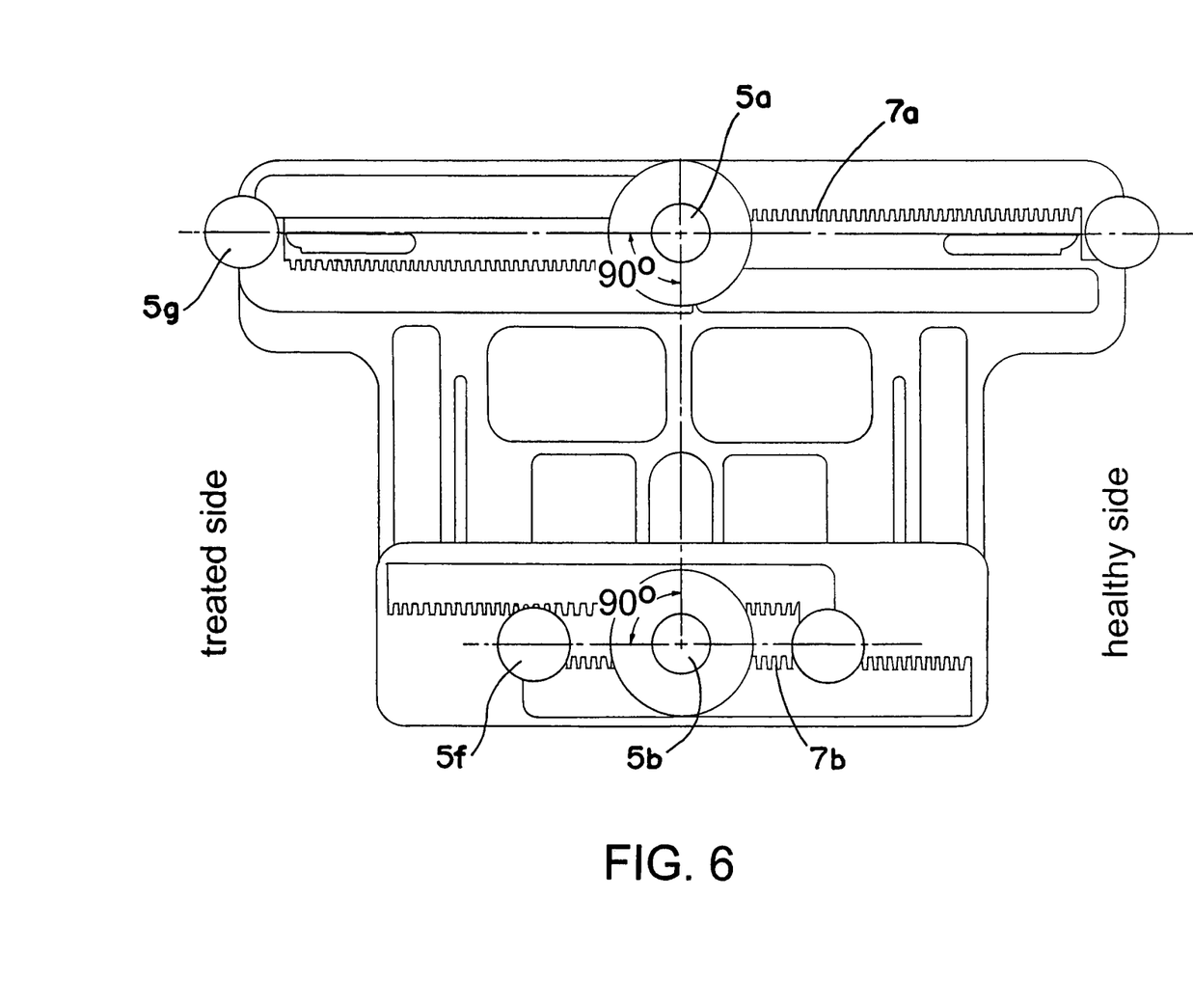

FIG. 6 shows an embodiment that includes four markers, wherein two markers 5a and 5b are arranged on the adjusting elements 7a and 7b and two markers 5f and 5g are arranged on the positioning elements 4a and 4c of one side. Using the device shown, it is possible to detect the mid-sagittal plane, a spinal point and a pubic point on the side to be treated, wherein a detection system or software detects four individual markers that advantageously lie on a plane which lies parallel to the contact points of the positioning elements. As defined, the mid-sagittal plane is perpendicular to this plane, wherein the position and the orientation of the mid-sagittal plane is additionally determined by the two markers arranged in the middle of the device. The four markers define two right angles. The position of the spinal and pubic points on the side to be treated are known if the length of the positioning elements 4a and 4c used (on which the markers 5f and 5g are arranged) is known. The spinal and pubic point on the healthy side not to be treated can be ascertained by mirroring the position of the spinal and pubic points on the mid-sagittal plane, detected via the positioning elements 4a and 4c.

Figure 7:
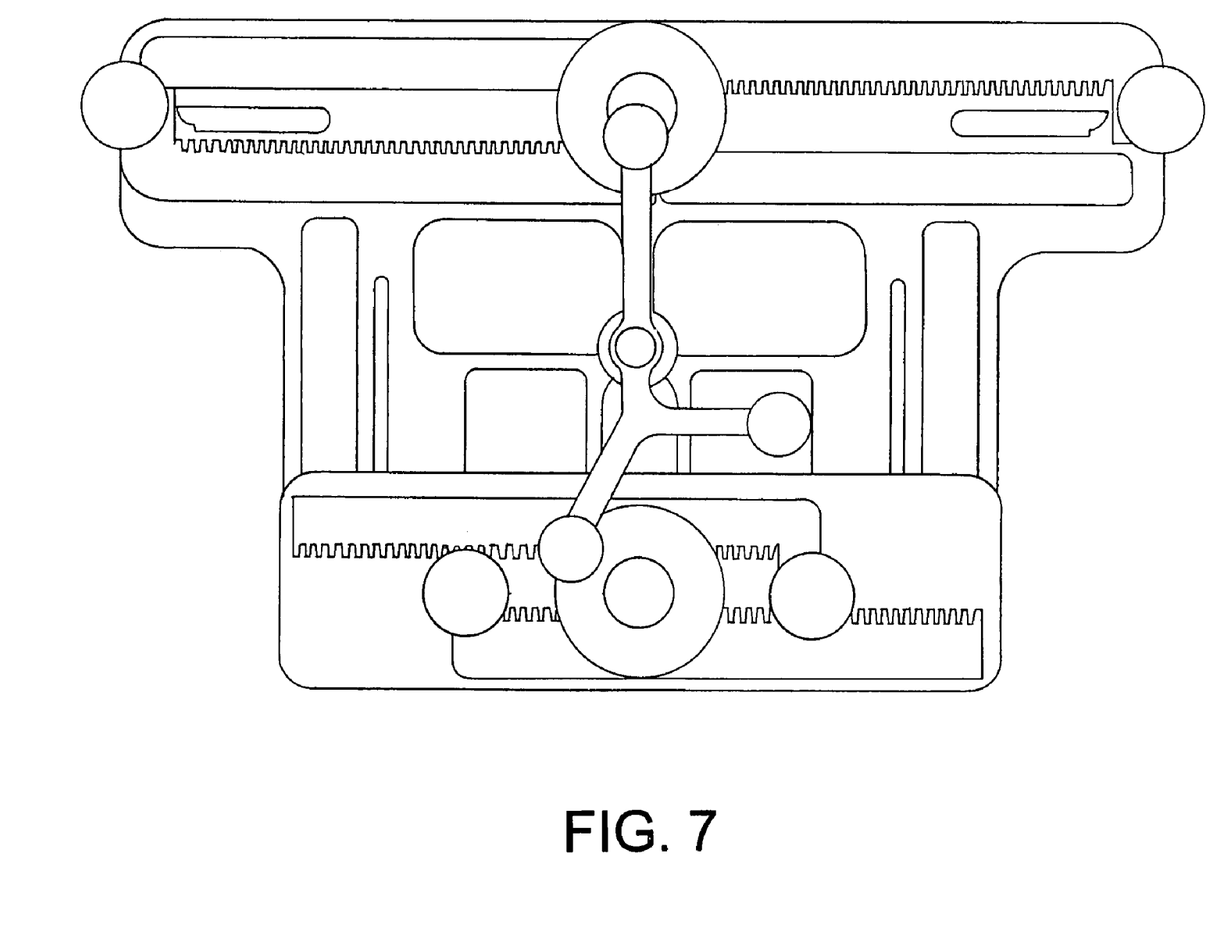
FIG. 7 is a top view of the device in accordance with the first embodiment, during a setting procedure.

FIG. 7 shows a third embodiment in accordance with the invention, including a reference star, wherein only two hip planes can be detected using the embodiment shown, such that a user has to detect at least two other landmarks in order to register the hip.

Figure 8:
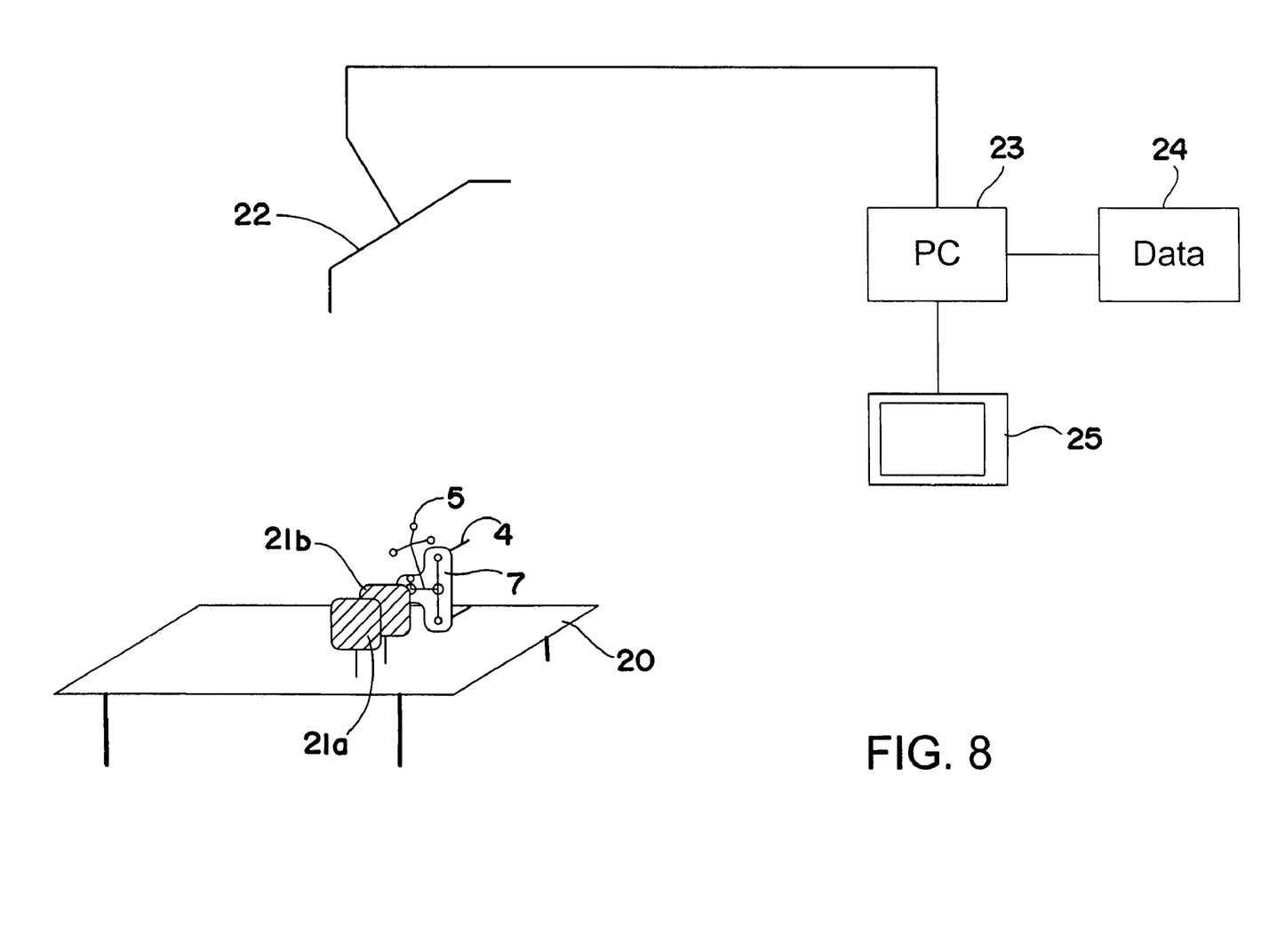
FIG. 8 illustrates a system in accordance with the invention.

FIG. 8 shows a table 20 with padded plates 21a and 21b arranged on the table 20. A patient can be held between the plates 21a and 21b in a lateral position. If the patient is fixed in the lateral position by the plates 21a and 21b, the patient's hip can be registered by the registration device 1 placed on the patient, wherein the position of the markers connected to the registration device 1 is detected by an infrared camera 22. The infrared camera 22 relays the position of the markers 5 to a computational unit 23, which is supplied with information on the geometry of the registration device 1 from a database 24. The computational unit 23 calculates the position of the tips of the positioning elements 4 of the registration device 1 to obtain the data for hip registration. Information for registering the hip can be output on a screen 25, for example, as shown in FIG. 9, wherein the position of the mid-sagittal plane and the pelvic inlet plane can be shown.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A device for registering a patient's hip while the patient is in a lateral position, comprising:
   a support;
   a plurality of positioning elements mounted to the support for movement relative to an immediately adjacent portion of the support, said plurality of positioning elements configured for placement on characteristic points of the hip;
   at least one adjusting element operatively coupled to at least two positioning elements of the plurality of positioning elements, wherein movement of the at least one adjusting element effects a corresponding movement of the at least two positioning elements relative to the immediately adjacent portion of the support; and
   markers operatively connected to respective ones of the positioning elements, said markers being trackable by a navigation system, wherein movement of the at least two positioning elements relative to the immediately adjacent portion of the support effects a corresponding movement of the respective markers, whereby when the positioning elements have been placed on characteristic points of the hip, data for registering the hip can be ascertained from the position of the markers.

2. The device as set forth in claim 1, wherein at least one positioning element is a rod.

3. The device as set forth in claim 1, wherein the adjusting element is configured to effect simultaneous movement of two positioning elements, said simultaneous movement of the positioning elements being movement parallel to each other.

4. The device as set forth in claim 3, wherein movement of the adjusting element effects simultaneous movement of at least two the positioning elements in opposite directions.

5. The device as set forth in claim 1, wherein the markers are passive markers.

6. The device as set forth in claim 1, wherein the markers are reflective markers.

7. The device as set forth in claim 1, wherein a reference star is connected to the device, and a star plane of the reference star is parallel to a plane defined by contact points of the positioning elements.

8. The device as set forth in claim 1, wherein at least one marker is connected to a positioning element and/or the at least one adjusting element.

9. The device as set forth in claim 1, wherein an angle formed between a first group of markers fixed to the device and a second group of markers is 90 degrees.

10. The device as set forth in claim 1, wherein at least one marker is connected to the device via an adjustable marker array.

11. A system for registering a hip of a patient while the patient is in a lateral position, comprising:
    a device as set forth in claim 1;
    a detection unit for detecting a position of the markers of the device; and
    a computational unit communicatively coupled to the detection unit, said computational unit configured to ascertain information for registering a hip on which the device can be placed, said information based on a geometry of the device.

12. The device according to claim 1, wherein the positioning elements are formed as elongated members having a longitudinal axis, the positioning elements arranged such that the longitudinal axes are parallel to each other.

13. The device according to claim 12, wherein the positioning elements comprise a first pair of positioning elements and a second pair of positioning elements, and a line formed between distal ends of the first pair of positioning elements is parallel to a line formed between distal ends of the second pair of positioning elements.

14. The device according to claim 1, wherein the support includes at least one guide, and the positioning elements are configured to move along a path defined by the at least one guide.

15. The device according to claim 14, wherein the at least one guide comprises a first guide and a second guide, the first guide arranged perpendicular to the second guide.

16. The device according to claim 14, wherein the guide is formed as a slot in the support.

17. The device according to claim 1, wherein the at least one adjusting element is configured such that rotational movement of the at least one adjusting element effects linear movement of the at least two positioning elements.

18. A device for registering a patient's hip while the patient is in a lateral position, comprising:
    a support;
    a plurality of positioning elements mounted to the support for movement relative to an immediately adjacent portion of the support, at least one positioning element of said plurality of positioning elements movable relative to another positioning element of said plurality of positioning elements so as to enable the plurality of positioning elements to be placed on characteristic points of the hip;
    at least one adjusting element operatively coupled to at least two positioning elements of the plurality of positioning elements, wherein movement of the at least one adjusting element effects a corresponding movement of the at least two positioning elements relative to the immediately adjacent portion of the support; and a plurality of markers trackable by a navigation system, wherein at least one marker of said plurality of markers is operatively connected to said at least one positioning element, wherein movement of said at least one positioning element relative to the immediately adjacent portion of the support effects a corresponding movement of the at least one marker, whereby when the positioning elements are placed on characteristic points of the hip, data for registering the hip can be ascertained from the position of the markers.

19. The device according to claim 18, wherein the positioning elements comprise at least three positioning elements, each of said at least three positioning elements corresponding to a different characteristic point on the hip.

20. The device according to claim 18, wherein said at least one adjusting device is adapted to effect symmetrical movement of the at least two positioning elements of the plurality of positioning elements.

21. The device according to claim 18, wherein said at least one adjusting device is adapted to effect movement of at least one positioning element relative to other positioning elements of the plurality of positioning elements.

22. The device according to claim 18, wherein the at least one adjusting element is configured such that rotational movement of the at least one adjusting element effects linear movement of the at least two positioning elements.

* * * * *